United States Patent
Stauffer

(10) Patent No.: US 6,933,414 B1
(45) Date of Patent: Aug. 23, 2005

(54) ACETONE PROCESS

(76) Inventor: John E. Stauffer, 6 Pecksland Rd., Greenwich, CT (US) 06831

( * ) Notice: Subject to any disclaimer, the term of this patent is extended or adjusted under 35 U.S.C. 154(b) by 82 days.

(21) Appl. No.: 10/870,971

(22) Filed: Jun. 21, 2004

(51) Int. Cl.$^7$ .............................................. C07C 45/61
(52) U.S. Cl. ...................... 568/388; 568/392; 568/393; 568/411
(58) Field of Search ................................ 568/388, 392, 568/393, 411

(56) References Cited

U.S. PATENT DOCUMENTS

| | | | | |
|---|---|---|---|---|
| 1,821,324 A | * | 9/1931 | Roka | 260/134 |
| 1,891,333 A | * | 12/1932 | Meerwein et al. | 260/134 |
| 1,892,742 A | * | 1/1933 | Walter et al. | 260/134 |
| 1,944,109 A | * | 1/1934 | Roka | 568/388 |
| 3,547,783 A | * | 12/1970 | Yamaguchi et al. | 203/37 |
| 6,331,654 B1 | * | 12/2001 | Zakoshansky et al. | 568/411 |

OTHER PUBLICATIONS

Kirk–Othmer. Encyclopedia of Chemical Technology, 4th Ed., John Wiley & Sons, New York 1991, pp. 180–184.

* cited by examiner

*Primary Examiner*—Johann Richter
*Assistant Examiner*—Sikarl A. Witherspoon
(74) *Attorney, Agent, or Firm*—Patton Boggs LLP

(57) ABSTRACT

A process is provided for the production of acetone from formaldehyde and methyl chloride. In the process formaldehyde is reacted in the vapor phase with methyl chloride to produce acetone and hydrogen chloride. Acetaldehyde may be formed as an intermediate in the reaction. The byproduct hydrogen chloride may be recovered from the process to produce additional methyl chloride from methyl alcohol.

6 Claims, 3 Drawing Sheets

ACETONE PROCESS

FIELD OF THE INVENTION

The present invention relates to a process for the manufacture of acetone from formaldehyde and methyl chloride. Formaldehyde is reacted with methyl chloride in the vapor phase to produce acetone and byproduct hydrogen chloride. Acetaldehyde may be an intermediate in the reaction.

BACKGROUND OF THE INVENTION

Although numerous processes have been used in the past to manufacture acetone, today most of the world's acetone is obtained as a coproduct of phenol production by the cumene process. In this process benzene is alkylated with propylene to produce cumene, which in turn is oxidized to cumene hydroperoxide. The latter compound is cleaved to yield phenol and acetone.

Acetone not produced by the cumene process is obtained primarily by the dehydrogenation of isopropyl alcohol. This reaction, which requires a catalyst, is straightforward and reportedly gives good yields. The necessary isopropyl alcohol feed generally is produced from propylene.

Thus, almost the entire world production of acetone is dependent on propylene as a hydrocarbon source. Since propylene is produced from natural gas liquids or refinery streams, its price has shown considerable volatility. This instability has impacted the economics of acetone manufacture.

Therefore, the object of the present invention is to minimize the disadvantages of existing commercial processes for acetone. One priority is to free producers from their dependence on propylene. Another goal is to provide a process in which acetone is the primary product. Additionally, high efficiency is a target of any new technology. These and other objects, features, and advantages will be apparent from the following description.

SUMMARY OF THE INVENTION

In one particular embodiment of the invention, formaldehyde is reacted with methyl chloride in the vapor phase to produce acetone and hydrogen chloride. Acetone is separated from the reaction products, by distillation or other commonly known separation processes, to provide the desired product.

The process must be carried out at sufficiently high temperatures in order to initiate the chemical reaction. These temperatures may be in the range of approximately 400° C. to approximately 600° C. The process is operated essentially at one atmosphere pressure, but higher pressures up to about 10 bar may be employed to reduce the size of the equipment.

The conversion of formaldehyde to acetone will depend on such variables as residence time, temperature, and the proportion of methyl chloride in the feed stream. In the process, formaldehyde is first converted to acetaldehyde, which is further reacted to acetone. Alternatively, acetone may be produced directly from formaldehyde. By modifying the process conditions, acetaldehyde may be produced as a coproduct of acetone.

DETAILED DESCRIPTION OF THE PROCESS

The process of the present invention encompasses entirely new chemistry. One molecule of formaldehyde (HCHO) reacts with two molecules of methyl chloride ($CH_3Cl$) to form one molecule of acetone ($CH_3COCH_3$) and two molecules of hydrogen chloride (HCl). This reaction takes place in the gas phase at elevated temperatures. The reaction can be represented by the following equation.

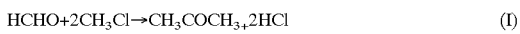

$$HCHO + 2CH_3Cl \rightarrow CH_3COCH_3 + 2HCl \quad (I)$$

The conversion of formaldehyde to acetone by the above chemistry quite probably takes place in two steps. First, formaldehyde reacts with methyl chloride to give acetaldehyde ($CH_3CHO$) and hydrogen chloride. Second, the acetaldehyde so formed in the first step reacts with additional methyl chloride to produce acetone and more hydrogen chloride. These two reactions can be given by the following two equations.

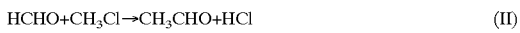

$$HCHO + CH_3Cl \rightarrow CH_3CHO + HCl \quad (II)$$

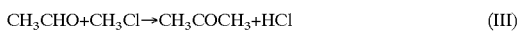

$$CH_3CHO + CH_3Cl \rightarrow CH_3COCH_3 + HCl \quad (III)$$

When equations (II) and (III) are combined, the result is identical to equation (I) above.

Under the conditions of the process, the reactions of equations (II) and (III) go essentially to completion. Thus, the overall reaction of equation (I) also goes to completion. The equilibrium constants for each of these three reactions can be determined from thermodynamic data for the enthalpies and Gibbs energies of formation of each of the reactants and products.

Figure 1:
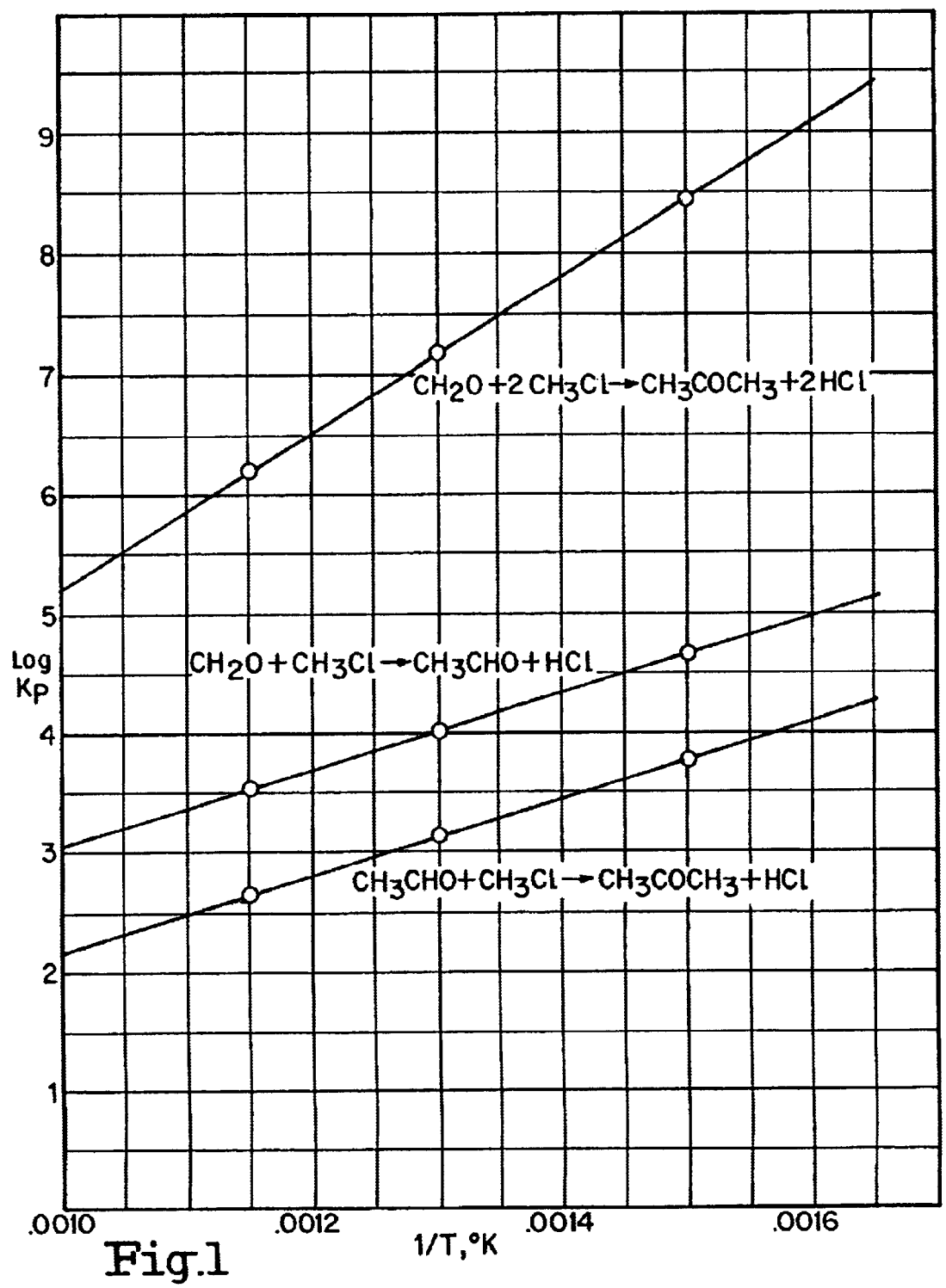
FIG. 1 is a diagram showing $K_P$ plotted as a function of the reciprocal of the absolute temperature T.

The results of these calculations show that the logarithm of the equilibrium constant $K_P$ for the reaction in equation (I) is equal to 8.41 at 400° C., 7.14 at 500° C., and 6.19 at 600° C. Likewise log $K_P$ for the reaction in equation (II) is 4.65 at 400° C., 4.01 at 500° C., and 3.53 at 600° C. Finally, log $K_P$ for equation (III) is 3.77 at 400° C., 3.13 at 500° C., and 2.66 at 600° C. These data are plotted in FIG. 1, which shows log $K_P$ as a function of the reciprocal of the absolute temperature T. These graphs can be used to determine equilibrium conditions at other temperatures.

A viable process must have favorable reaction kinetics. The process of the present invention depends on a series of free radical reactions at elevated temperatures to achieve high rates of reaction. These free radical reactions can be represented by the following equations.

$$CH_3Cl \rightarrow CH_3\cdot + Cl\cdot \quad (IV)$$

$$HCHO + Cl\cdot \rightarrow CHO\cdot + HCl \quad (V)$$

$$CHO\cdot + CH_3Cl \rightarrow CH_3CHO + Cl\cdot \quad (VI)$$

In the above reactions, equation (IV) represents the initiator that generates free radicals at the start. Both equations (V) and (VI) are the chain reaction steps. When equations (V) and (VI) are combined, the result is the same as equation (II).

Other sets of free radical reactions are involved in the formation of acetone. Thus, the following chain reactions are postulated.

$$CH_3CHO + Cl\cdot \rightarrow CH_3CO\cdot + HCl \quad (VII)$$

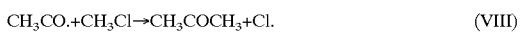

$$CH_3CO\cdot + CH_3Cl \rightarrow CH_3COCH_3 + Cl\cdot \quad (VIII)$$

Again, when equations (VII) and (VIII) are combined, the result is identical to equation (III).

Concomitantly, the process may proceed by the following reaction mechanism.

$$HCHO + Cl \cdot \rightarrow CHO \cdot + HCl \qquad (IX)$$

$$CHO \cdot + CH_3Cl \rightarrow CH_3CO \cdot + HCl \qquad (X)$$

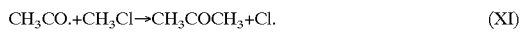

$$CH_3CO \cdot + CH_3Cl \rightarrow CH_3COCH_3 + Cl \cdot \qquad (XI)$$

In the above set of chain reactions, equation (IX) is the same as equation (V), and equation (XI) is the same as equation (VIII). When all three equations (IX), (X), and (XI) are combined, the net reaction is given by equation (I). In this case acetaldehyde is not produced as an intermediate.

The free radical reactions given by equations (IV) through (XI) are premised on bond dissociation energies for the constituent atoms, which contribute to high selectivity during the free radical reactions, especially under pyrolytic conditions. Thus, the chlorine atom attached to the carbon atom in methyl chloride has a bond energy of 339 kJ per mol whereas the hydrogen bond energy is 423 kJ per mol. Furthermore, the hydrogen atom on the carbonyl group in acetaldehyde has a bond energy of 364 kJ per mol while the hydrogen atoms attached to the methyl group each have a bond energy of 393 kJ per mol. This difference explains why the hydrogen atom on the carbonyl group will be preferentially substituted. Additionally, to vary the desired reaction kinetics and conversion ratios of the products, other halogen atoms, such as bromine, iodine, and astatine may be substituted to produce the reactants $CH_3Br$, $CH_3I$, and $CH_3At$. Furthermore, other organic groups may be substituted for the methyl group to vary the desired reaction kinetics and desired conversion ratios of the products.

The process of the present invention must be carried out at sufficiently high temperatures to overcome the bond energies involved with the free radical reactions. These temperatures may be in the range of 400° C. to 600° C., but this range is not meant to be limiting. Thus, at temperatures above 600° C., the reactions will occur, but the formation of byproducts can be excessive. At temperatures below 400° C., the rate of reaction will be slowed.

The control of the reaction temperature is considered to be important to the success of the process. As is the case with other free radical reactions, the desired temperature will depend on the residence time of the reactants in the reactor. Shorter residence times will require higher temperatures to achieve equal conversions per pass.

Figure 3:
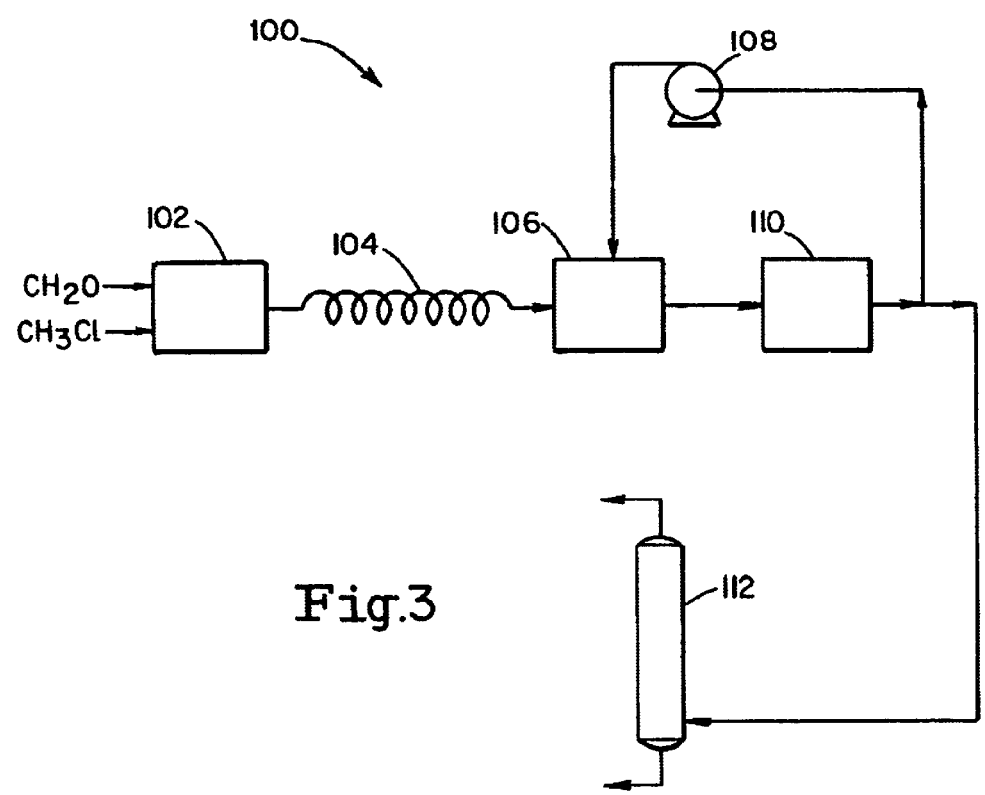
FIG. 3 is a block diagram depicting a simplified arrangement to control the process.

The fact that the reactions are exothermic complicates the control of the process. In one aspect of the present invention, the process includes several commonly known process units to control the process. Referring to FIG. 3 is a block diagram depicting a simplified arrangement 100 of process units to control the process. A substantial quantity of heat is generated during the process. Unavoidably the temperature of the reactants will increase as the reactions progress. In this aspect, the feed stream $CH_2O$ and $CH_3Cl$ are fed into the preheater 102 to heat the feed streams to a sufficiently high temperature to initiate the reactions. The feed streams are then fed into the reactor 104. By using a tubular design for the reactor 104, (the process is continuous as opposed to batch processes) the residence time can be most effectively controlled. The exit gases from the reactor 104 are quenched in a quench tower 106, for example by a liquid stream of acetone, to produce a liquid stream of the crude product. The crude product is then optionally fed into a heat exchanger 110 for further temperature control of the crude products. A slip stream of crude products can be fed into the quench tower 106 via pump 108. After exiting the heat exchanger 110, the crude products can be fed into a distillation unit 112 to separate the acetone from the other products contained in the product stream as described above. Optionally, a heater may be employed between the heat exchanger 110 and the distillation unit 112 to further provide proper distillation temperature of the acetone.

As is the experience with controlling other exothermic reactions, temperature control may be effected by modifying the concentrations of the reactants. Accordingly, hydrogen chloride gas might be recycled to the feed stream. In addition, pressures in excess of one atmosphere may be employed to economize on equipment size. A practical limit would be in the neighborhood of 10 bar.

Effective use of the byproduct hydrogen chloride from the process greatly influences the attractiveness of the present invention. The most likely application for this byproduct is to regenerate methyl chloride from methyl alcohol. Thus, not only is methyl alcohol the starting material for methyl chloride, but it is also used to produce formaldehyde. In effect, the net reactant requirement is methyl alcohol. This commodity is widely available, and it is produced in huge quantities from natural gas.

The present invention achieves the desired objective of freeing the manufacture of acetone from a reliance on propylene. Cl chemistry is used to provide a process that can be integrated all the way back to natural gas and air as the only raw materials. The term "Cl chemistry" is commonly used to describe chemical reactions involving organic compounds that contain only one carbon atom. The potential savings by this route are considerable. Lower cost acetone could greatly expand the markets for this critical petrochemical.

EXAMPLE

Figure 2:
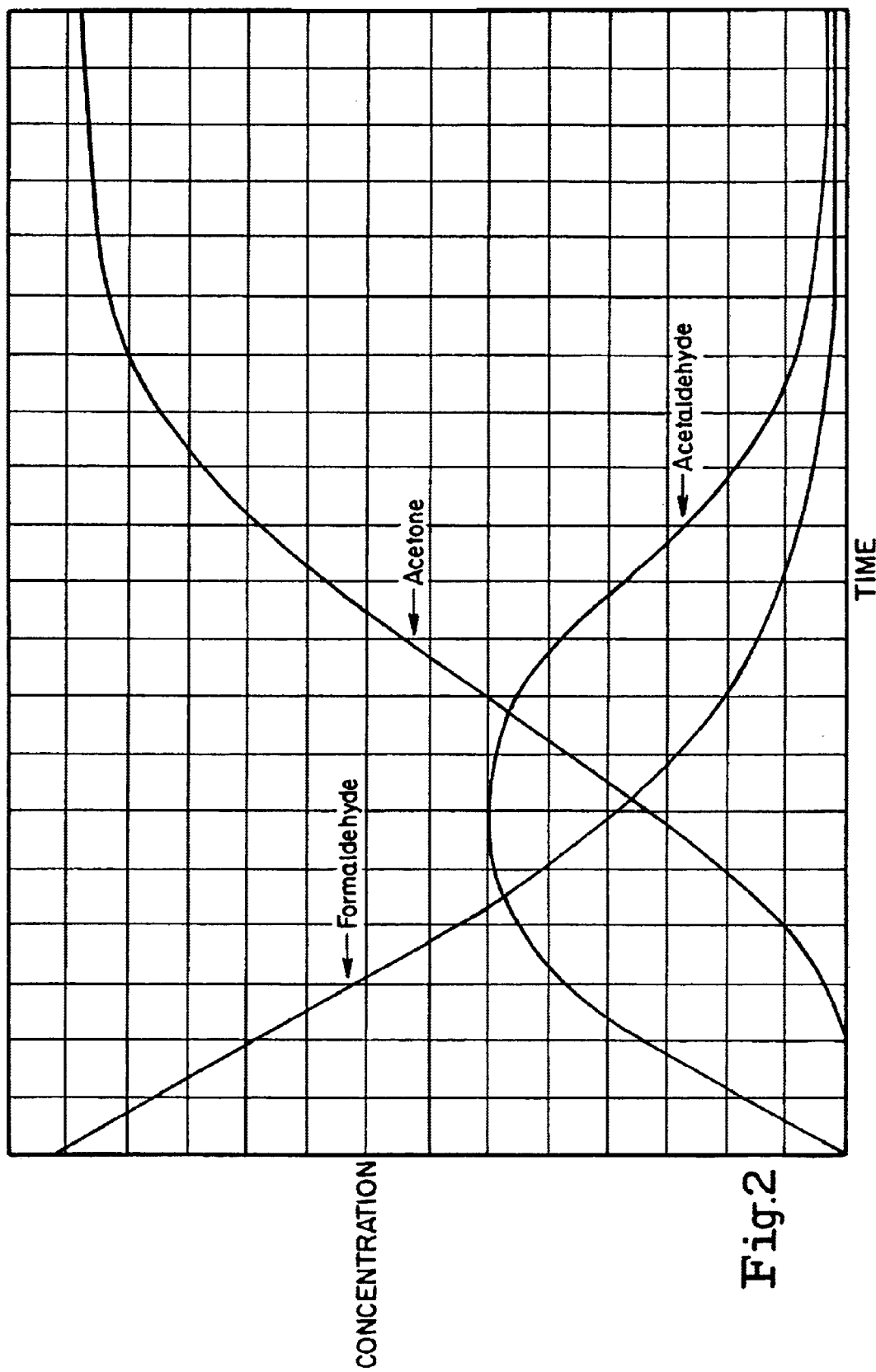
FIG. 2 is a diagram in which concentrations in the mol fraction are plotted as a function of resistance times % in the reaction.

Using engineering calculations based on reaction kinetics and stoichiometry, the data shown in FIG. 2 were developed. In this diagram, concentrations in mol fraction are plotted as a function of residence time, % in the reactor. Thus, the proportions of formaldehyde, acetaldehyde and acetone in the exit gas stream can be ascertained for any given conversion of formaldehyde. In this example, the concentration of formaldehyde in the feed stream was 33 mol percent, the balance being methyl chloride. When 50 percent of the formaldehyde was consumed, the product stream contained approximately 13.5 mol percent acetaldehyde and 3 mol percent acetone. When 98 percent of the formaldehyde was reacted, the product stream contained about 2 mol percent acetaldehyde and 30 mol percent acetone.

What is claimed is:

1. A process for the production of acetone comprising the reaction of formaldehyde with methyl chloride to give acetone and hydrogen chloride.

2. A process according to claim 1 in which the reaction is conducted in the vapor phase.

3. A process according to claim 1 in which the reaction is conducted at a temperature of about 400° C. to about 600° C.

4. A process according to claim 1 in which the reaction is conducted at a pressure in the range of 1 atmosphere to 10 atmospheres.

5. A process according to claim 1 in which hydrogen chloride is recycled to the reaction step.

6. A process according to claim 1 further comprising separating said acetone from said hydrogen chloride.

* * * * *